(12) United States Patent
Liu et al.

(10) Patent No.: US 8,043,507 B2
(45) Date of Patent: Oct. 25, 2011

(54) ION CHROMATOGRAPHY SYSTEM USING CATALYTIC GAS ELIMINATION

(75) Inventors: Yan Liu, Palo Alto, CA (US); Christopher A. Pohl, Union City, CA (US); Nebojsa Avdalovic, Cupertino, CA (US); John M. Riviello, Santa Cruz, CA (US); Archava Siriraks, Bangkok (TH)

(73) Assignee: Dionex Corporation, Sunnyvale, CA (US)

( * ) Notice: Subject to any disclaimer, the term of this patent is extended or adjusted under 35 U.S.C. 154(b) by 985 days.

(21) Appl. No.: 11/955,083

(22) Filed: Dec. 12, 2007

(65) Prior Publication Data

US 2008/0116139 A1 May 22, 2008

Related U.S. Application Data

(62) Division of application No. 11/065,335, filed on Feb. 23, 2005, now Pat. No. 7,329,346.

(51) Int. Cl.
*B01D 15/08* (2006.01)

(52) U.S. Cl. ............... 210/635; 210/656; 210/198.2; 205/789; 422/70

(58) Field of Classification Search ............ 210/635, 210/638, 656, 659, 748, 198.2, 243; 422/70; 205/789, 792.5
See application file for complete search history.

(56) References Cited

U.S. PATENT DOCUMENTS

| | | | |
|---|---|---|---|
| 3,230,046 A | 1/1966 | Beroza | |
| 5,045,204 A | 9/1991 | Dasgupta et al. | |
| 5,248,426 A | 9/1993 | Stillian et al. | |
| 5,352,360 A | 10/1994 | Stillian et al. | |
| 6,027,643 A | 2/2000 | Small | |
| 6,036,921 A | 3/2000 | Small et al. | |
| 6,093,327 A | 7/2000 | Anderson, Jr. et al. | |
| 6,225,129 B1 | 5/2001 | Liu et al. | |
| 6,315,954 B1 | 11/2001 | Liu et al. | |
| 6,316,270 B1 | 11/2001 | Liu et al. | |
| 6,316,271 B1 | 11/2001 | Liu et al. | |
| 6,558,551 B1 | 5/2003 | Anderson, Jr. et al. | |
| 6,562,628 B1 | 5/2003 | Liu et al. | |
| 6,682,701 B1 | 1/2004 | Liu et al. | |
| 7,473,354 B2* | 1/2009 | Liu et al. | 210/198.2 |
| 7,585,679 B1* | 9/2009 | Liu et al. | 436/161 |
| 2004/0048389 A1 | 3/2004 | Liu et al. | |

(Continued)

FOREIGN PATENT DOCUMENTS

EP 0 555 962 A2 8/1993

(Continued)

OTHER PUBLICATIONS

Hoffman, R., "Döbereiner's lighter," *Am. Sci. Online* 86(4):326 (Jul.-Aug. 1998).
Kim, Y.J., "Effect of noble metal addition on electrochemical polarization behavior of $H_2$ oxidation and $O_2$ reduction on 304SS in high-temperature water," *GE Res. Dev. Ctr.* 97CRD203, Class 1 (Feb. 1998).
Owens, G., et al., "Demonstrating catalysis with a bang!," *Chem. Educator* 1(4):1-4 (1996).

(Continued)

*Primary Examiner* — Ernest G Therkorn
(74) *Attorney, Agent, or Firm* — Morgan, Lewis & Bockius, LLP; David J. Brezner; Gregory C. Ellis

(57) ABSTRACT

A liquid chromatographic system is provided including catalytically combining hydrogen and oxygen gases in the chromatography eluent stream in a catalytic gas elimination chamber, to form water and thereby reduce the gas content in the eluent stream. Also, a liquid ion chromatographic system in which the effluent from the detector is recycled to a membrane suppressor and then is mixed with a source of eluent for recycle to the chromatographic column.

3 Claims, 5 Drawing Sheets

U.S. PATENT DOCUMENTS

2007/0062873 A1    3/2007    Liu et al.

FOREIGN PATENT DOCUMENTS

| | | |
|---|---|---|
| EP | 1 205 750 | 5/2002 |
| WO | WO 98/32011 A1 | 7/1998 |
| WO | WO 99/56849 | 11/1999 |

OTHER PUBLICATIONS

Sobczyk, D.P., et al., "Activation of ammonia dissociation by oxygen on platinum sponge studied with positron emission profiling," *J. Catalysis* 219(1):156-166 (Oct. 2003).

\* cited by examiner

ION CHROMATOGRAPHY SYSTEM USING CATALYTIC GAS ELIMINATION

CROSS-REFERENCE TO RELATED APPLICATIONS

This application is a divisional application of pending U.S. patent application Ser. No. 11/065,335, filed on Feb. 23, 2005.

BACKGROUND OF THE INVENTION

Since it was introduced in 1975, ion chromatography has become a widely used analytical technique for the determination of anionic and cationic analytes in various sample matrices. In ion chromatography, dilute solutions of acids, bases, or salts are commonly used as the electrolytes in chromatographic eluents. Traditionally, These eluents are prepared off-line by dilution with reagent-grade chemicals. Off-line preparation of chromatographic eluents can be tedious and prone to operator errors, and often introduces contaminants. For example, dilute NaOH solutions, widely used as the electrolytes in eluents in the ion chromatographic separation of anions, are easily contaminated by carbonate. The preparation of carbonate-free NaOH eluents is difficult because carbonate can be introduced as an impurity from the reagents or by adsorption of carbon dioxide from air. The presence of carbonate in NaOH eluents often compromises the performance of an ion chromatographic method, and can cause an undesirable chromatographic baseline drift during the hydroxide gradient and even irreproducible retention times of target analytes. Therefore, there is a general need for convenient sources of high purity acid, base, or salt for use as eluents in the ion chromatographic separations.

A number of approaches that utilize the electrolysis of water and charge-selective electromigration of ions through ion-exchange media have been investigated by researchers to purify or generate high-purity ion chromatographic eluents.

U.S. Pat. No. 5,045,204 describes that an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

U.S. Pat. Nos. 6,036,921, 6,225,129, 6,316,271, 6,316,270, 6,315,954, and 6,682,701 describe electrolytic devices that can be used to generate high purity acid and base solutions by using water as the carrier. Using these devices, high purity, contaminant-free acid or base solutions are automatically generated on-line for use as eluents in chromatographic separations. These devices simplify gradient separations that can now be performed using electrical current gradients with minimal delay instead of using a conventional mechanical gradient pump. The use of high-purity eluents generated by the electrolytic eluent generators can significantly improve the performance of ion chromatographic methods.

United States Patent Application No. 2004/0048389 describes electrolytic devices for generating salt solutions. In these devices, an acid or base is generated in an aqueous solution by the steps of: (a) providing a source of first ions adjacent an aqueous liquid in a first acid or base generation zone, separated by a first barrier (e.g., anion exchange membrane) substantially preventing liquid flow and transporting ions only of the same charge as said first ions, (b) providing a source of second ions of opposite charge adjacent an aqueous liquid in a second acid or base generation zone, separated by a second barrier transporting ions only of the same charge as the second ions, and (c) transporting ions across the first barrier by applying an electrical potential through said first and second zones to generate an acid-containing aqueous solution in one of said first or second zones and a base-containing aqueous solution in the other one which may be combined to form a salt solution such as a solution of potassium carbonate. The advantages of using these electrolytic devices for eluent generation in ion chromatography were demonstrated.

The continuous operation of an ion chromatography system can consume a significant amount of eluents. The consistent preparation of such large amount of the eluent as well as the disposal of the used eluent can pose serious logistical challenges to the system operators in terms of costs and labor, especially in cases where unattended or less frequently attended operations are required. Even though it overcomes a number of issues associated conventional approaches of eluent preparation in ion chromatography, the use of on-line electrolytic eluent generation devices still requires a constant supply of high purity water from an external source for continuous operation and waste disposal issue remains.

To simplify ion chromatographic operations, minimize waste disposal, and reduce operating costs, it would be advantageous to provide a system capable of recycling prepared eluent or water used in the electrolytic eluent preparation.

SUMMARY OF THE INVENTION

In one embodiment of the invention, a chromatographic method is provided including the steps of (a) injecting sample ionic species into an aqueous eluent stream, (b) chromatographically separating said sample ionic species in said eluent stream by flowing the same through chromatographic separation medium, (c) detecting said separated sample ionic species in said eluent stream effluent from said chromatographic medium; and (d) catalytically combining hydrogen and oxygen gases, or catalytically decomposing hydrogen peroxide, or both, in said eluent stream in a catalytic gas elimination chamber, to form water and reduce the gas content in said eluent stream.

In another embodiment, a chromatographic method is provided comprising the steps of (a) chromatographically separating sample ionic species in an aqueous liquid eluent stream flowing through a chromatography separation medium, to form a chromatography effluent, (b) suppressing the chromatography effluent from step (a) by flowing it through a chromatography effluent flow channel on one side of a first ion exchange membrane in a membrane suppressor, (c) flowing suppressor effluent from the chromatography effluent flow channel past a flow-through detector to form a detector effluent stream, (d) recycling the detector effluent from step (c) to a detector effluent flow channel in the membrane suppressor on the opposite side of the first membrane from the chromatography effluent flow channel, and (e) mixing effluent from the detector effluent flow channel with a source of eluent and flowing the mixture to the chromatography separation medium.

In other embodiments of the invention, apparatus is provided capable of performing the above methods.

DETAILED DESCRIPTION OF THE INVENTION

The system of the present invention is useful for determining ionic species which are solely anions or cations. Suitable liquid samples include surface waters, other liquids such as industrial chemical waste, body fluids, beverages or drinking water. The term "ionic species" includes molecular species in ionic form and molecules which are ionizable under the conditions of the present invention. The term "eluent" refers to the solution flowing in a liquid chromatography system which carries a sample to be detected. At times herein, the term eluent also refers to the electrolyte in that solution. The eluent normally is water-based but can include an organic solvent so long as it is electrochemically stable.

In certain embodiments, the invention includes a suppressor. The purpose of a suppressor is to reduce the conductivity and noise of the analysis stream background while enhancing the conductivity of the analytes (i.e., increasing the signals/noise ratio), while maintaining chromatographic efficiency.

Figure 1:
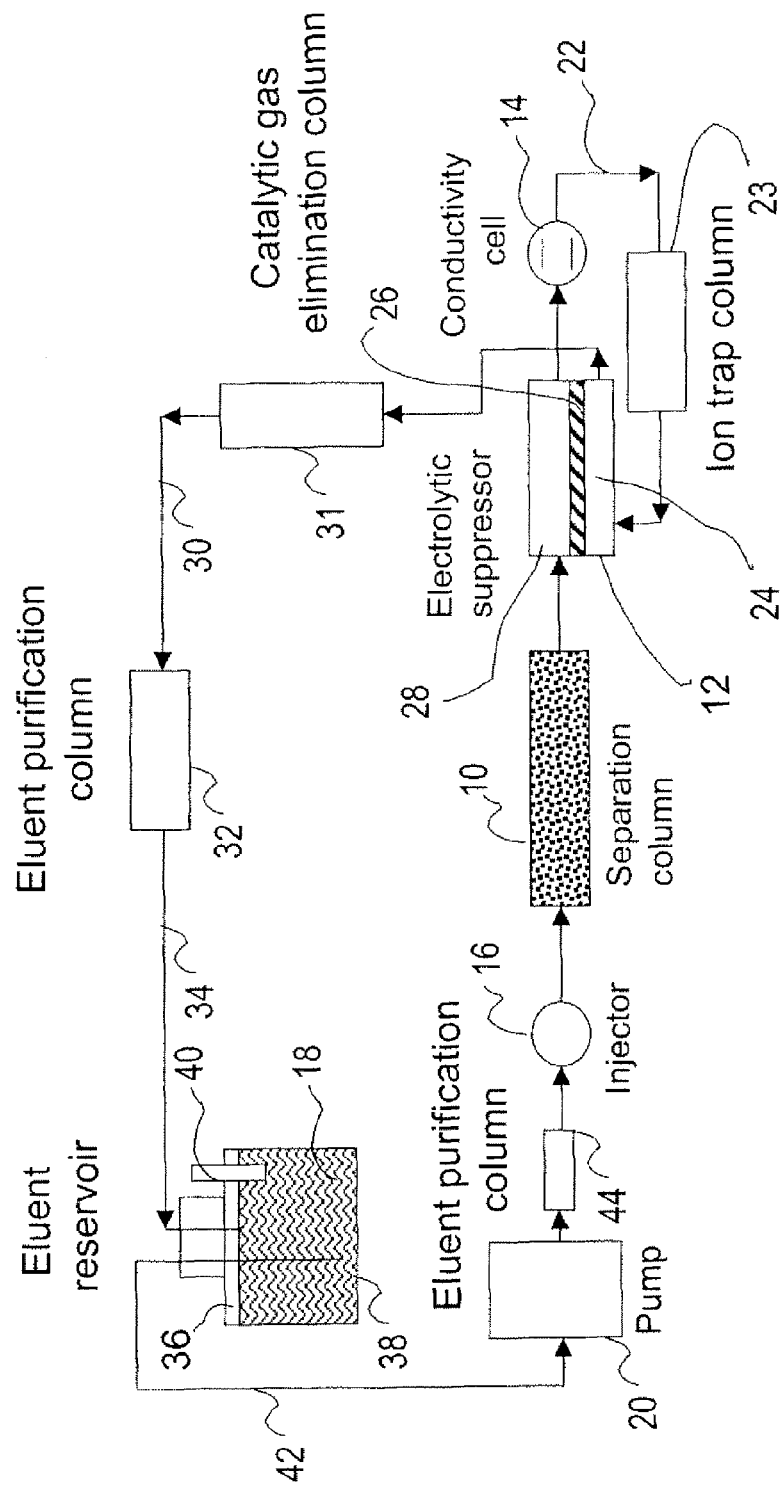
FIGS. 1, 2 and 3 are schematic representations of apparatus according to different embodiments of the present invention.

Referring to FIG. 1, a simplified apparatus for performing the present invention is illustrated. This system includes a suppressor with recycle of the effluent from a detector to the suppressor. That portion of the system is similar to the general system illustrated in U.S. Pat. No. 5,248,426. One important difference of the system of FIG. 1 from that patent is that the effluent from the suppressor is recycled to the separation column, preferably after mixed with an eluent in an effluent reservoir, as part of the eluent electrolyte used for separation. In a preferred embodiment, one or more eluent purification columns such as ion trap columns are used in the system to remove contaminants, typically in ionic form, in the recycled stream prior to use as an eluent in the separation column.

Referring specifically to FIG. 1, the system includes chromatographic separation medium, typically in the form of chromatographic separation medium chromatographic column 10. (As used herein, the term "column" refers to a flow-through housing with an interior chamber in any configuration for performing the indicated function.) Any known chromatographic separation medium may be employed including ion exchange resin, a porous hydrophobic chromatographic resin permanently attached to ion exchange sites, and medium used for mobile phase ion chromatography (MPIC).

Arranged in series with column 10 is a suppressor 12 serving to suppress the conductivity of the electrolyte of the eluent from column 10 but not the conductivity of the separated ions. The effluent from suppressor 12 is directed to a detector, preferably in the form of a detector flow-through conductivity cell 14, for detecting the ion species resolved in column 10. A suitable sample including ion species is supplied through sample injection valve or injector 16 which is passed through the apparatus in the solution of eluent from an eluent source or reservoir 18 drawn by pump 20 which then passes through injection valve 16. The chromatography effluent solution leaving column 10 is directed through suppressor 12 wherein the electrolyte is converted to a weakly conducting form. The chromatography effluent from suppressor 12 passes through detector 14, schematically illustrated as a conductivity cell, in which the presence of ionic species produces an electrical signal proportional to the amount of ionic material. Such a signal is typically directed from detector 14 to a conductivity meter (not shown). Any other known detector useful for detecting ionic species in a chromatography system may also be employed including absorbance and electrochemical detectors.

In one embodiment, the effluent from conductivity detector 14, referred to as the detector effluent, is directed in a recycle conduit 22 to at least one flow-through detector effluent flow channel 24 in suppressor 12. An ion exchange membrane 26 separates detector effluent flow channel 24 from chromatographic separation effluent flow channel 28 which receives the effluent from chromatography column 10. In the simplified version illustrated, only a single detector effluent flow channel 24 is used. The system of the present invention is also applicable to other membrane suppressors such as the sandwich suppressor type illustrated in U.S. Pat. No. 5,248,426. In a sandwich suppressor, the chromatographic separation effluent flows through a central flow channel flanked by two detector effluent flow channels separated by ion exchange membranes. In this embodiment, the detector effluent flow channels may be supplied with the detector effluent from conductivity detector 14 by use of a splitter valve. The details of such a sandwich suppressor and the use of recycle from the conductivity cell are supplied by the detector effluent flow channel as illustrated in U.S. Pat. No. 5,248,426. As illustrated, for anion analysis, the detector effluent flow channel is positively charged and hydronium ions are generated for passage through membrane 26 according to the following equation:

$$6H_2O \rightarrow 4H_3O + O_2 + 4e^- \quad (1)$$

In the chromatography effluent flow channel, cations of the electrolyte, e.g., sodium ions, pass through membrane 26 into the effluent of the cathode for electrolytic suppressor. Hydroxide is converted to water according to the following equation:

$$OH^- + H_3O^+ \rightarrow 2H_2O \quad (2)$$

Figure 3:
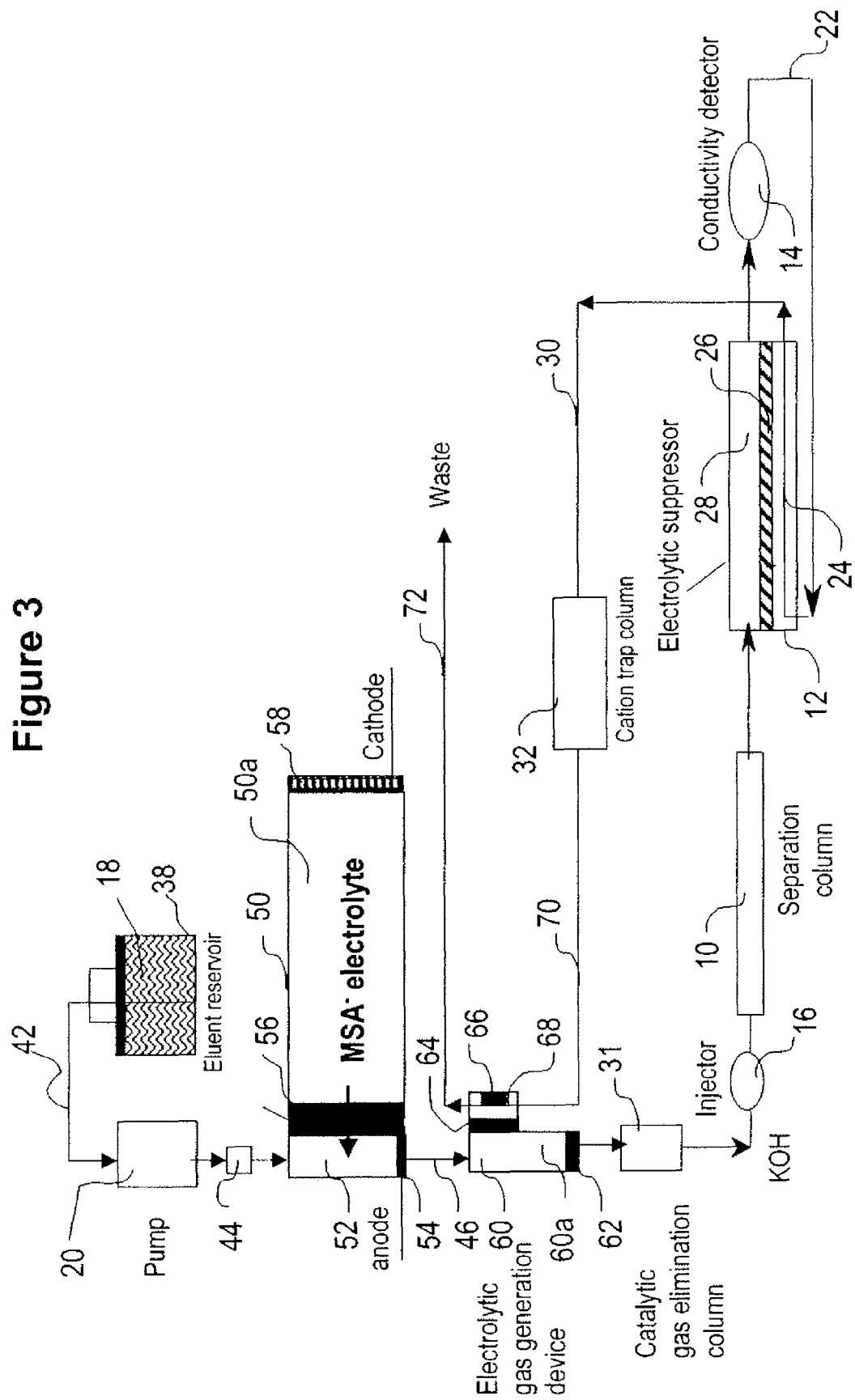
Figure 4:
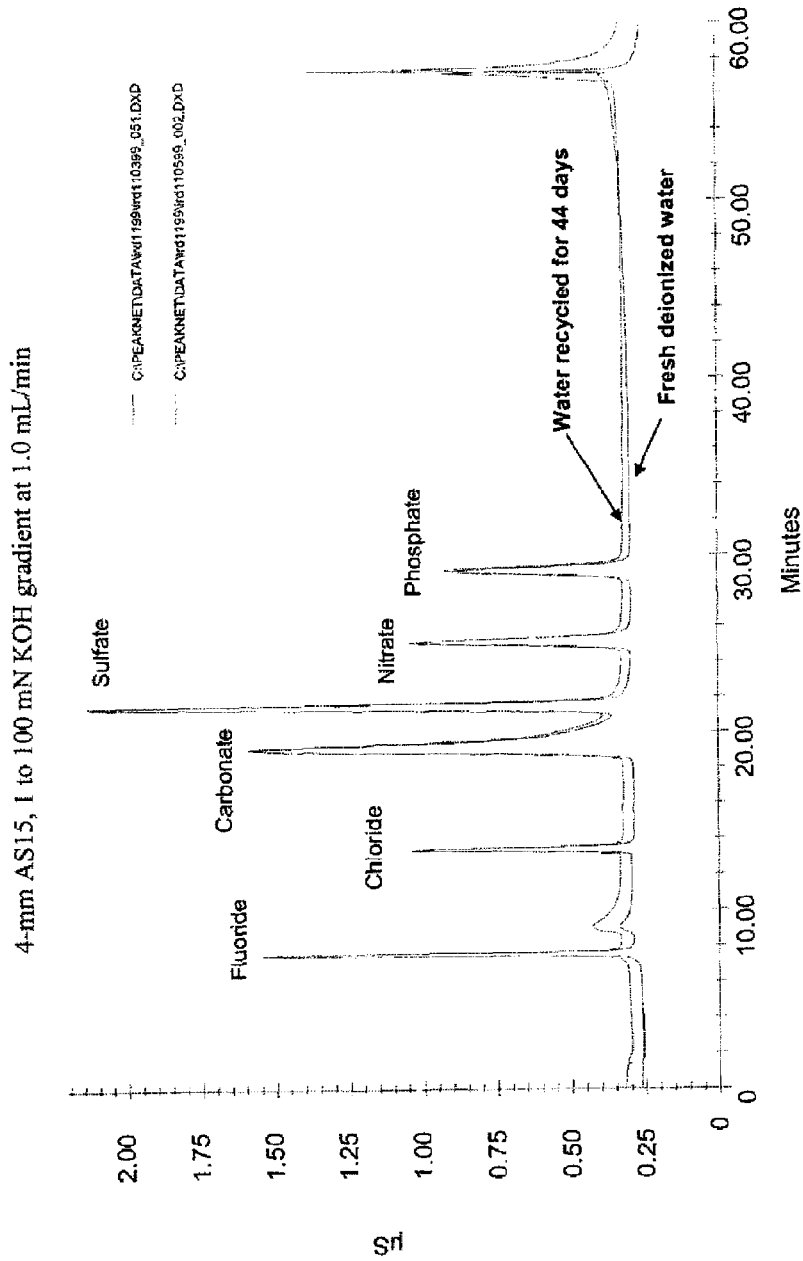
FIGS. 4 and 5 are chromatograms illustrating experimental results using the present invention.

In a preferred embodiment, the suppressor is of the electrolytic type as illustrated in FIGS. 3 and 4 of U.S. Pat. No. 5,352,360.

Suitable eluent solutions for anion ion chromatography include alkali hydroxides, such as sodium hydroxide, alkali carbonates and bicarbonates, such as sodium carbonate, alkali borates, such as sodium borate, combinations of the above, and the eluent systems of the aforementioned patents.

The recycle system of the present invention is also applicable to the analysis of cations (e.g., lithium, sodium, ammonium, potassium, magnesium, and calcium). In this instance, the electrolyte of the eluent is typically an acid which does not damage the membrane. Methane sulfonic acid has been found to be inert to the membrane under electrolytic conditions. Other acids such as nitric acid and hydrochloric acid produce electrochemical by-products that may damage the membrane and are, thus, not generally preferred for that typical membrane.

In the effluent recycle system of U.S. Pat. No. 5,248,426, the effluent from the detector effluent flow channel is directed to waste. In contrast, in the system of FIG. 1, the effluent is redirected to the separation column 10, preferably by flow through the eluent reservoir 18.

Referring specifically to FIG. 1, the effluent from the detector effluent channel flows in line 30 through optional catalytic gas elimination column 31 and optional eluent purification column 32 and from there through tubing projecting through a closure 36 of container 38 of eluent reservoir 18. An optional gas vent 40 is provided in reservoir container 38 to vent hydrogen and oxygen gases which are generated electrolytically in the system. Eluent solution from reservoir 18 is directed in line 42 to separation column 10 as the source of eluent for separation. As illustrated, the eluent in line 42 flows through pump 10 and optional eluent purification column 44 prior to separation column 10.

Also as illustrated in FIG. 1, optional ion trap column 23 can be placed in line 22 between conductivity cell 14 and suppressor 12. Preferably, the ion trap column 23 is packed with anion exchange resin in carbonate form for anion analysis using carbonate eluents or anion ion exchange resin in the hydroxide form for anion analysis using hydroxide eluents. Typically, it only removes ions of one charge, positive or negative. For cation analysis using acid eluents, the ion trap column may be packed with cation exchange resin in the hydronium form. The ion trap column serves the function for retaining analyte ions in the suppressed eluent.

For a system in which eluent is recycled from the detector to the separation column, it is preferable to remove contaminants of sample injected through injection valve 16, and other trace contaminants may be generated from operation of the ion chromatography system. This can be performed by using one or both of purification columns 32 or 44. One form of eluent purification column preferably includes an inlet section and an outlet section, not shown, with a strongly acidic cation exchange material, e.g., resin in the inlet section, preferably in the form of the cation of the eluent used. For example, the resin preferably in the form of sodium for a sodium carbonate eluent or in the hydronium form for a sulfuric acid eluent. The outlet section may be packed with strongly basic cation exchange material, e.g., resin in the form of the anion of the flowing eluent. For example, the form may be carbonate for the sodium carbonate eluent or sulfate for the sulfuric acid eluent. It is preferable to use highly cross-linked and macroporous high area for both the cation exchange resin and the anion exchange resin used in purification columns. It is preferable to use resins having cross-linking of at least 20%, preferably at least 30% and surface area of at least 10 m$^2$/g, preferably at least 20 m$^2$/g. Such resins are effective in removing components of the injected sample and other trace contaminants generated in the system. Examples of such resins include AG MP-50 strongly acidic cation exchange resin and AG MP-1M strongly basic anion exchange resin available from Bio-Rad (Hercules, Calif.). Other forms of optional eluent purifiers may be employed.

Optionally, the eluent purification columns 32 or 44 may also include an additional section of neutralized porous resin, preferably of high surface area to remove non-charged contaminants in the recycle eluent. In the illustrated embodiment, a larger eluent purification column 32 is placed upstream of suppressor 12 in comparison to the optional smaller purification column 44 placed at the outlet of pump 20 to further purify the eluent prior to entering separation column 10. If the second purification column 44 is used, it preferably has about 50% or less of the capacity of the purification column 32. Suitably, column 32 has an ion exchange capacity of at least 0.5 milliequivalents.

In general, the eluent purification column and the ion trap column remove the ions from the sample injected and some trace components derived at the system. When the purified eluent is recycled back into eluent reservoir 18, the solution typically contains a mixture of electrolytically generated hydrogen gas and oxygen gas. Some of these gases may be removed from the eluent reservoir 18 equipped through a gas vent port 36.

In a preferred embodiment, a catalytic gas elimination column 31, including an internal flow-through chamber, is used to remove hydrogen and oxygen gases in an eluent chromatography system which recycles eluent from a detector for reuse. In one embodiment, column 31 is provided in line 30 or 34 before or after column 32.

It is useful to discuss the principles of operation of a catalytic gas elimination chamber typically contained in a flow-through housing termed a column herein. Even though the combination of hydrogen and oxygen to form water is an exothermic process, hydrogen and oxygen do not react automatically when mixed together. The reason for this is the relatively large activation energy needed to begin the reaction. The mechanism is somewhat complex. It is a free radical mechanism with one of the initiation steps is:

$$H_2(g) \rightarrow 2H\cdot(g) \tag{3}$$

Breaking the bond between the two hydrogen atoms requires 432 kJ/mole. This energy can be initially provided by a spark or a flame. After the reaction begins, the produced energy provides the necessary energy to continue breaking apart the hydrogen molecules. A catalyst provides an alternative mechanism that has a lower activation energy, this allows the reaction to proceed without the requirement of the initial addition of energy such as a flame or spark.

Platinum is known to catalyze the reaction of hydrogen and oxygen. (Nature, vol. 390, 495-497, 1997; Journal of Chemical Physics, vol. 107, 6443-6447, 1997; Surface Science, vol. 324, 185-201, 1995.) If platinum is placed into a container filled with hydrogen and oxygen, the platinum begins to glow as it heats up, and water droplets condense in the container. Cooling the platinum so that it doesn't just ignite the mixture provides a smooth conversion of the hydrogen and oxygen to water. This reaction occurs because platinum provide a new route for the reaction. In this new pathway, hydrogen molecules react with the platinum atoms on the surface of platinum. This reaction breaks the H—H bond and forms two Pt—H bonds. The energy of activation for this process is small. Oxygen reacts with these Pt—H groups to form water, again, with a very small energy of activation. Through this low energy route for the reaction, platinum catalyzes the recombination of oxygen and hydrogen gases. The term "catalyst" encompasses any catalyst that performs this function. Platinum is described as one specific example of such a catalyst.

The above principles of using the known property of a catalyst such as platinum to catalytically induce the reaction between hydrogen gas and oxygen gas to form water provide the basis for the catalytic gas elimination chamber of the present invention for use in liquid chromatography. This permits the elimination of these gaseous electrolysis byproducts of an electrolytic suppressor in the eluent in a system like FIG. 1. In such a system, the effluent from the outlet of the electrolytic suppressor regenerant chamber 24 is passed through the catalytic gas elimination column 31, where the hydrogen and oxygen present in the effluent react catalytically to form water. Column 31 may be packed with a suitable catalyst such as pure Pt in metal particle, mesh, or foil form. Alternatively, the column may also be packed with other inert substrates coated with Pt. In the present invention, optional catalytic gas elimination column 31 serves several important functions. First, it provides an elegant means to conveniently eliminate the build up hydrogen and oxygen gases and thus facilitates the operation of continuous eluent recycle. Second, the water-forming reaction of hydrogen and oxygen is expected to be stoichiometric in the column, and the amount of water formed is expected to be in principle the same as the amount of water that is originally consumed to produce hydrogen and oxygen gases in the electrolytic operation of the suppressor. In principle, this feature eliminates an increase in the concentration of eluent due to the consumption of water in the electrolytic operation of the suppressor. Third, the Pt catalytic gas elimination column also serves the function to catalytically decompose trace levels of hydrogen peroxide which may be formed during the electrolytic operation of the suppressor. The presence of hydrogen peroxide in the recycled eluent is potentially detrimental since it may attack the ion exchange functional groups in the separation column and the eluent purification column in the system and degrade the column performance. The use of Pt to catalyze the decomposition of hydrogen peroxide is well known (Bull. Korean Chem. Society, 1999, vol. 20(6), 696; U.S. Pat. No. 6,228,333).

The catalytic gas elimination chamber may have a wide variety of physical forms. One embodiment uses a chromatographic column housing with fritted flow-through end fittings that are used to retain either pure Pt metal particles, mesh, or foils packed inside the column. The column may also be packed with other inert substrates coated with Pt. In a preferred embodiment, the internal diameter of the column is 0.1 mm or larger and the length of the column is 0.5 cm or longer. It is preferred to use Pt packing material in forms that provide high surface area to increase its catalytic efficiency. It is also preferred to operate the catalytic gas elimination chamber in flow rates ranging from 0.1 uL/min to 50 mL/min although other flow rates may be used.

A number of systems are known for practicing eluent recycling in chromatography systems and ion chromatography systems. U.S. Pat. No. 6,027,643 discloses a method and apparatus for electrolytically generating an acid or base in an aqueous solution and for simultaneously suppressing conductivity of the eluent in an ion exchange bed after chromatographic separation in an ion chromatography system. U.S. Pat. No. 6,562,628 teaches a combination of electrolytic suppressor and separate eluent generator and method for use such devices in an ion chromatography system. U.S. Pat. Nos. 6,093,327 and 6,558,551 describe several different embodiments of electrolytic devices and their uses in ion chromatography. Since deionized water is used as the preferred carrier stream in some embodiments of ion chromatography systems disclosed, the above patents describe that the spent water can be recycled after passing through an ion exchange water polisher column. However, these patents do not address the potential problems associated with the presence of hydrogen and oxygen gases in the spent stream of the water to be recycled.

Figure 2:
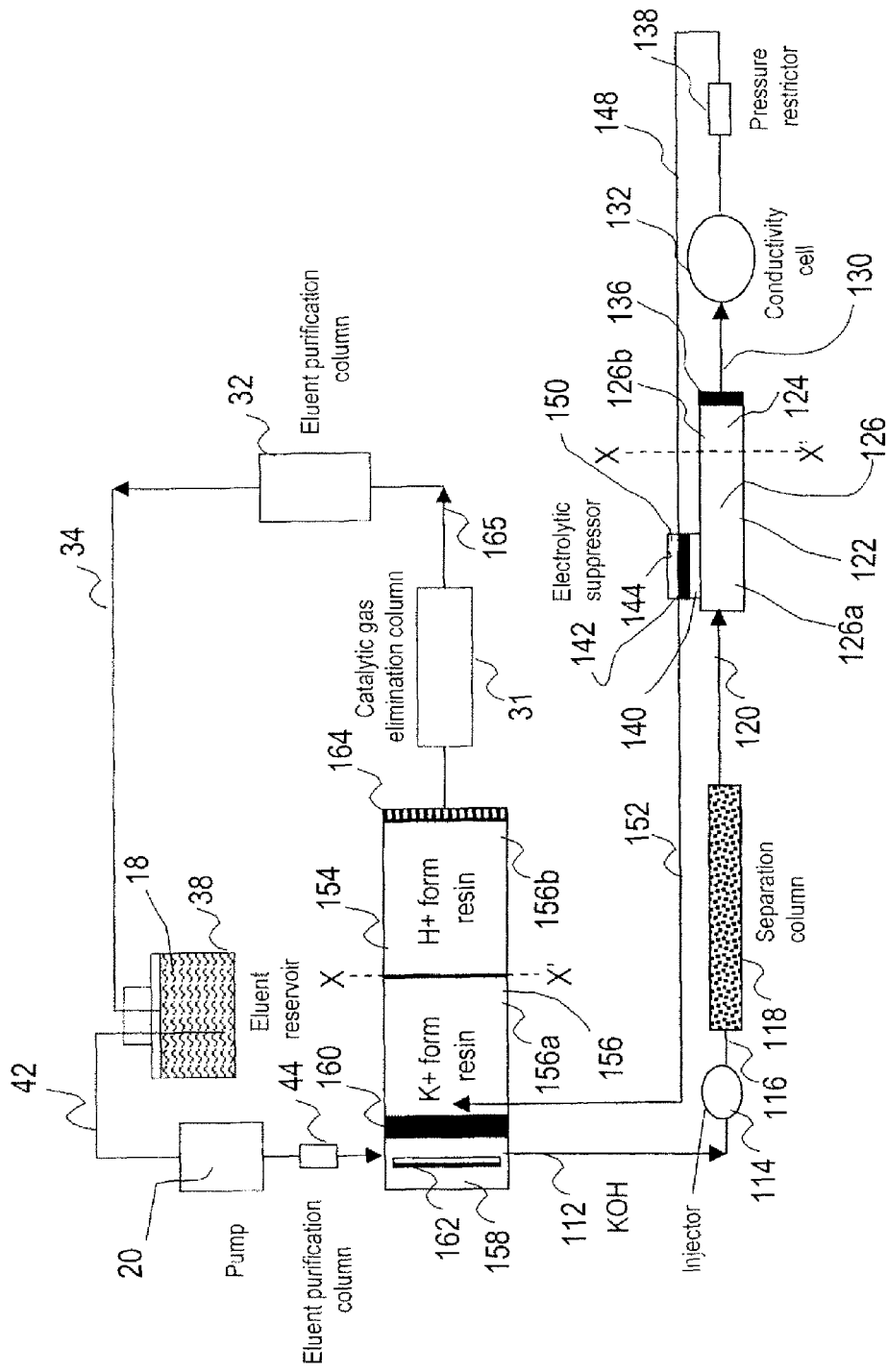

Referring specifically to FIG. 2, an ion-reflux based chromatography system using water recycle is illustrated using the principles and the same system as FIG. 1 of U.S. Pat. No. 6,562,628 with certain differences. A catalytic gas elimination column, an eluent reservoir, and an eluent purification column have been added. A pump for the eluent from the reservoir is illustrated. Further, optional degaser 56 is not shown. The system first will be briefly described with respect to the common elements of FIG. 1 of the '628 patent and FIG. 2 herein, followed by a description of the added elements.

The system of FIG. 2 illustrates improved methods to recycle water in an ion chromatography system through the use of a catalytic gas elimination column, preferably in combination with water purification columns. It illustrates the combined use of water purification columns and the catalytic gas elimination column for recycling water in an ion-reflux based ion chromatography system that generates and recycles potassium hydroxide eluents for anion analysis. The detailed functions of the electrolytic eluent generation and recycle module and electrolytic suppressor have been disclosed in the '628 patent. In this ion chromatography system, the deionized water is used as the preferred carrier stream in the electrolytic generation and recycle of potassium hydroxide eluent. The effluent from the outlet of the eluent generation and recycle module is a mixture of water, hydrogen gas, oxygen gas, and possibly some trace components derived from the operations of the entire ion-reflux based ion chromatography system. To recycle the water, the effluent from the eluent generation and recycle module is first passed through the catalytic gas elimination column to eliminate hydrogen and oxygen gases. Since stoichiometric amounts of hydrogen and oxygen gases are generated in the electrochemical processes occurring in the electrolytic eluent generation and recycle module and the electrolytic suppressors, it is expected that hydrogen and oxygen combine to form water in the same amount that is originally consumed. The effluent from the catalytic gas elimination column is then passed through the water purification column to remove the remaining trace ionic and non-ionic contaminants. The purified water is routed back to the water reservoir.

The additional components in FIG. 2 herein compared to FIG. 1 of the '628 patent are similar in structure and function to the corresponding components in the embodiment of FIG. 1 herein. Thus, like parts will be designated with like numbers and the descriptions of such components will apply.

Referring specifically to FIG. 2, the solution leaving the eluent generator in line 165 flows through catalytic gas elimination column 31, through an eluent purification column 32 (corresponding to polishing column 67 in FIG. 1 of the '628 patent) through line 34 into container 38 for eluent reservoir 18. The recycled solution in line 34 is mixed in eluent reservoir 18 and is directed via pump 20 in line 42 through a second eluent purification column 44. (A vent pipe in reservoir 18 is not illustrated because hydrogen and oxygen gases may be eliminated in column 31.) From there on, the system is as described above.

In a similar manner, a catalytic gas elimination column may be advantageous used in any other chromatography system, such as referred to above, in which the detector effluent is recycled as a source of eluent liquid.

Referring again to FIG. 2, an ion chromatography system is illustrated using a continuous electrolytically regenerated packed bed suppressor (CERPBS) form of suppressor and one embodiment of the eluent generator. The system includes an analytical pump 20 connected by tubing 112 to sample injection valve 114 which in turn is connected by tubing 116 to a flow-through chromatographic separator 118 typically in the form of a chromatographic column packed with chromatographic resin particles. The effluent from chromatographic column 118 flows through tubing 120 to a packed ion exchange resin bed flow-through suppressor 122. Typically, suppressor 122 is formed of a column 124 packed with an ion exchange resin bed 126 of the type used for ion chromatography suppression. Electrodes are spaced apart in the suppressor, with at least one electrode separated from the resin by a barrier described below. The electrodes are connected to a direct current power supply, not shown. The configuration is such that with an aqueous stream flowing through the suppressor and the application of power, water in the aqueous stream is electrolyzed to form a source of hydronium ion or hydroxide ion to continuously regenerate the ion exchange resin bed during the analysis.

The suppressor effluent is directed through tubing 130 to a suitable detector 132 and then eventually to waste. A preferred detector is a conductivity detector with a flow-through conductivity cell. The chromatography effluent flows through the cell.

Suppressor 122 generates hydronium ions (and oxygen gas) at the anode and hydroxide ions (and hydrogen gas) at the cathode. That is, a water-containing eluent solution including electrolyte is directed from the pump and through tubing 112. Sample is injected through sample injection valve 114, and is directed by tubing 116 into chromatographic column 118 to form a first chromatography effluent including separated ionic species of the sample. For simplicity of description, unless otherwise specified the system will be described with respect to the analysis of anions using an eluent solution including sodium hydroxide as the electrolyte.

A suitable sample is supplied through sample injection valve 114 which is carried in a solution of eluent supplied from pump 20. Anode 136 is disposed at the outlet end of resin bed 126 in intimate contact with the resin therein. The effluent from bed 126 is directed to a detector suitably in the form of a flow-through conductivity cell 132 of the conductivity detector (not shown), for detecting the resolved anions in the effluent, connected to a conductivity meter.

In the detector, discussed regarding FIG. 1, the presence of anions produces an electrical signal proportional to the amount of ionic material.

The system also includes an optional component for pressurizing the effluent from suppressor 122 prior to detection to minimize adverse effect of gases (hydrogen or oxygen) generated in the system as will be described hereinafter. As illustrated in FIG. 1, such pressurizing means comprises a pressure restrictor 138 downstream of conductivity cell 132 to maintain the ion chromatography system under pressure.

Column 124 is typically formed of plastic conventionally used for an ion exchange column. It has a cylindrical cavity of a suitable length, e.g., 60 mm long and 4 mm in diameter. It is packed with a high capacity cation exchange resin, e.g., of the sulfonated polystyrene type. The resin is suitably contained in the column by a porous frit which serves to provide an outlet to the column. In the illustrated embodiment, the porous frit is porous electrode 136 which serves the dual function of containment of the resin and as an electrode.

A barrier 140 separates bed 126 from electrode 142 in the interior of a hollow housing defining an ion receiving flow channel in electrode chamber 144 preventing any significant liquid flow but permitting transport of ions only of the same charge as the charge of exchangeable ions on resin bed 126. For anion analysis, barrier 140 is suitably in the form of a cation exchange membrane or plug separating electrode chamber 144 from the cation exchange resin.

A conduit 148 is provided to direct the aqueous liquid stream to the inlet 150 of electrode chamber 144. Conduit 152 takes the effluent from chamber 144 to the eluent generator. This provides a means of making electrical contact with the electrodes that is at the same time easy to seal against liquid leakage.

The line X-X is illustrated across the resin bed 126. For reasons which will be explained below, the resin upstream of the dotted line may be predominantly or completely in the form of the cation counter ion of the base used as the electrolyte during separation. Downstream of the line X-X, the resin may be predominantly or completely in the hydronium form. The line X-X represents the interface.

For anion analysis, a polarizing DC potential is applied between cathode 142 and anode 136, and the following reactions take place.

The water is electrolyzed and hydronium ions are generated at anode 136 according to the following reaction:

$$H_2O - 2e^- \rightarrow 2H^+ + \tfrac{1}{2}O_2\uparrow \qquad (4)$$

This causes cations in the cation exchange resin bed 126 to migrate to barrier 140. This, in turn, displaces hydronium ions upwardly through bed 126 which causes a similar displacement of cations ahead of them. The cations electromigrate toward the barrier 140 to be transported across the barrier 140 toward cathode 142 in cathode chamber 144 while water is electrolyzed at cathode 142 to generate hydroxide ions according to the following reaction:

$$2H_2O + 2e^- \rightarrow 2OH^- + H_2\uparrow \qquad (5)$$

The cations which have transported across the barrier combine with the generated hydroxide ions to form cation hydroxide in cathode chamber 144. The effluent from separator bed percolates through the cation form resin in inlet bed section 126 until it reaches the hydronium form resin in bed section 126 where it is neutralized while the cation is retained on the resin. At this point, the anion salts are converted to their respective acids and the cation hydroxide is converted to weakly ionized form, water.

The suppressed effluent liquid containing the separated anions leaves bed 126 through conduit 130 and passes to conductivity cell 132 in which the conductivity of the separated anions is detected.

The suppressor of FIG. 2 has been described with respect to a system for the analysis of anions. However, the system is also applicable to the analysis of cations. In this instance, electrode 136 is a cathode and electrode 142 is an anode. The ion exchange type of resin is reversed. Thus, the resin in separator bed 118 is a cation exchange resin and the resin in suppressor bed 126 is an anion exchange resin. The plug or membrane 140 is made of an anion exchange material.

Briefly described, the suppressor works as follows for the cation analysis. The aqueous liquid stream containing cations to be detected and an acid electrolyte aqueous eluent are directed through separator bed 118 including cation exchange resin. The effluent from separator bed 118 flows through suppressor bed 126 including anion exchange resin with exchangeable hydroxide ions. The acid in the eluent is converted to weakly ionized form. Some of the exchangeable hydroxide is displaced by anions from the acid.

An electrical potential is applied between the cathode 136 and anode 142. Water is electrolyzed at electrode 136 to generate hydroxide to cause anions on the anion exchange resin bed to electromigrate toward barrier 140 to be transported across the barrier toward the positively charged anode 142 in the ion receiving flow channel in electrode chamber 144 while water in chamber 144 is electrolyzed to generate hydronium ions which combine with the transported anions to form acid in the electrode chamber 144. The effluent liquid from the suppressor bed 126 flows past detector 132 in which separated cations are detected and is recycled to electrode chamber 144.

Referring again to FIG. 2, one embodiment of the eluent generator is illustrated, describing first the system for anion analysis in which a base generated in electrode chamber 144 is directed to the eluent generator. This embodiment is analogous in electrochemical operation to suppressor 124. In this embodiment of the eluent generator, a suitable housing 154 contains an electrolyte ion reservoir in the form of a packed bed of ion exchange resin 156. Resin bed 156 is separated from a first generator electrode chamber 158 by a charged generator barrier 160 which prevents significant liquid flow but permits transport of electrolyte ions and thus may be of the type described with respect to suppressor barrier 140. A generator electrode 162 is disposed and enclosed in generator electrode chamber 158 and may be of the same type of construction as electrode chamber 144. At the opposite side of barrier 160 from electrode 162 is flow-through generator electrode 164 analogous in function and structure to suppressor electrode 136.

The electrochemical reactions described above with respect to the suppressor occur in the eluent generator and so are incorporated herein by reference. Thus, for analysis of anions, the line x-x separates the inlet section 156a from the outlet section 156b of resin bed 156. The feed stream in line 152 flows into inlet section 156a in the cation form while the outlet section is in the hydronium ion form. However, one difference is that the feed stream in conduit 152 already includes base. The feed stream exits packed resin bed 156 adjacent barrier 160 and flows across bed 156 and out the outlet through electrode 164 or past some other form of electrode as described above. Similarly, the packed bed includes resin in the electrolyte ion form (e.g., potassium or sodium) at its inlet end adjacent barrier 160 and in hydrogen ion form near the outlet end adjacent electrode 164.

The same type of packed bed resin or other form of matrix may be used in the eluent generator as in the suppressor. As illustrated, the source of aqueous liquid flowing through generator electrode chamber 158 can be liquid recycled from the outlet of the resin bed chamber 154. Specifically, such liquid flows through conduit 165 and into a mixed (cation and anion exchange) bed water polishing column, or eluent purification column 32. This column is typically 2 to 40 cm in length and 0.5 to 10 cm in internal diameter. From there, the stream flows through conduit and flows to eluent reservoir 18. In the case of anion analysis, the cation hydroxide is generated in chamber 58 adjacent the cathode in the manner described above with respect to the suppressor. The water source after passing through the water polisher is deionized and so does not interfere with the analysis. An optional eluent purification column 44 may be placed after pump 20 to further purify the deionized water stream A chromatography system may generate non-stoichiometric quantities of $H_2$ or $O_2$ for full catalytic conversion in the catalytic gas elimination column. In another embodiment of the invention as illustrated in FIG. 3, a gas generation device, preferably an electrolytic one, may be placed on line to adjust the gases to stoichiometric amounts, thereby eliminating most or, preferably, substantially all of the hydrogen and oxygen gases in the eluent using the catalytic gas elimination column.

The system shown in FIG. 3 is illustrated using a methanesulfonic acid (MSA) eluent generator. It produces oxygen gas during the process of generating the MSA eluent. Oxygen gas in the MSA eluent stream leaving the eluent generator can be removed by passing the stream through a piece of permeable tubing of the type used in Dionex EG50 eluent generator degas module (Dionex Corporation, Sunnyvale, Calif. U.S.A.). In the system shown in FIG. 3, the stream of the MSA solution containing oxygen gas is passed through an electrolytic gas generator that is used to generate a stoichiometric amount of hydrogen gas relative to the amount of oxygen in the MSA eluent stream. The stream exiting the electrolytic gas generator is then passed through the catalytic gas elimination column where the stoichiometric amounts of hydrogen and oxygen gases react catalytically to form water. The MSA eluent stream leaving the catalytic gas elimination column is therefore substantially free of gas and may be used as the eluent in the ion chromatography system such as the one illustrated in FIG. 3.

Referring specifically to FIG. 3, like parts with FIGS. 1 and 2 are designated with like numbers. A carrier solution (e.g., deionized water) from the eluent reservoir 18 in the container 38 is directed via a pump 20 in line 42 through an eluent purification column 44 into the eluent generation chamber 52 of the electrolytic MSA eluent generator 50.

The construction of the electrolytic MSA generator can be similar to the type illustrated in FIG. 1 of the U.S. Pat. No. 6,225,129. The apparatus includes MSA ion source reservoir 50a that can be filled with a solution of MSA electrolyte. The MSA eluent generation chamber 52 is separated from the MSA ion source reservoir 50a by a barrier 56, suitably in the form of a charged perm-selective membrane described below. Barrier 56 substantially prevents liquid flow while providing an ion transport bridge for MSA ions from the ion source reservoir 50a to the MSA generation chamber 52. As used herein, the term "barrier" refers to the charged material (e.g. membrane) separating reservoir 50a and chamber 52 which permits ion flow but blocks substantial liquid flow, alone or in combination with an appropriate flow-through housing in which the barrier is mounted transverse to flow across the entire flow path. The charged barrier 56 should be of sufficient thickness to withstand the pressures in chamber 52. For example, if chamber 52 is on line with a chromatography system, such pressures may be on the order of 1,000 to 3,000 psi.

A cathode 58 is disposed in electrical contact with, and preferably within, MSA ion source reservoir 50a and an anode 54 is disposed in electrical contact with, and preferably within, base generation chamber 52. A suitable DC power supply (not shown) connects the anode and the cathode. Also, there is a continuous electrical path from anode 54 through barrier 56 to cathode 58.

For the production of pure acid (e.g. MSA), high-purity deionized water from the eluent purification column 44 is directed into to generation chamber 52. Water splitting takes place at both electrodes. The cathode reaction in reservoir 50a is as follows:

$$2H_2O + 2e^- \rightarrow 2OH^- + H_2\uparrow \tag{6}$$

During this reaction, the hydroxide ions are produced by the cathode in reservoir 50a. In one form of reservoir 50a, the ion source is a MSA-containing solution, suitably a methanesulfonic acid solution. In this manner, hydroxide ions react with hydronium ions to form water, methanesulfonate anion is the primary ion passing through barrier 56, thereby minimizing the flow of hydroxide ions. The reaction of hydronium ions and hydroxide ions in the reservoir provides electrical neutrality to the solution in the reservoir as the MSA ions are driven across the barrier 56 under the applied electrical field into the generation chamber 52 where hydronium ions are produced in the following anodic reaction.

$$H_2O - 2e^- \rightarrow 2H^+ + \tfrac{1}{2}O_2\uparrow \tag{7}$$

The combination of MSA ions and hydronium ions leads to production of acid (MSA) in the flowing aqueous stream. The concentration of MSA formed is directly proportional to the applied current and inversely proportional the flow rate.

The flowing aqueous solution from the eluent generation chamber contains MSA and oxygen gas. This mixture is then directed via line 46 into the electrolytic gas generator 50. The electrolytic gas generator 50 may be formed of a column 60 packed with a cation ion exchange bed 60a. Electrodes, in a form to be described below, are spaced apart in the electrolytic gas generator, with one electrode separated from the resin by a barrier described below. The electrodes are connected to a direct current power supply (not shown). The configuration is such that with an aqueous stream flowing through the electrolytic gas generator and the application of power, water in the aqueous stream is electrolyzed to form a source of hydrogen gas and hydroxide ions at the cathode and oxygen gas and hydronium ions at the anode.

Because of its ready availability and known characteristics, a preferred form of ion exchange bed 60a is a packed ion exchange bed of resin particles. It is desirable that the resin particles be tightly packed in the bed, to form a continuous ion bridge or pathway for the flow of ions between electrodes 62 and 66. Also, there must be sufficient spacing for the aqueous stream to flow through the bed without undue pressure drops.

The resin is suitably contained in the column by a porous frit which serves to provide an outlet to the column. In the illustrated embodiment, the porous frit is porous electrode 62 which serves the dual function of containment of the resin and as an electrode. Cathode 62 disposed at the outlet end of resin bed 60a preferably is in intimate contact with the resin therein.

A barrier 64 separates resin bed 62 from electrode 66 (anode) in the interior of a hollow housing defining electrode chamber 68 preventing any significant liquid flow but permitting transport of ions only of the same charge as the charge of exchangeable ions on resin bed 26. For generation of hydrogen gas at cathode 62, barrier 64 is suitably in the form of a cation exchange membrane or plug separating electrode chamber 68 from the cation exchange resin.

Electrode 66 in electrode chamber 68 also suitably is in the form of an inert metal (e.g., platinum) porous electrode in intimate contact with barrier 64. An electrode is fabricated in a way to permit good irrigation of the electrode/membrane interface when water is passed through electrode chamber 68. The electrode is suitably prepared by crumpling and forming a length of fine platinum wire so as to produce a roughly disc-shaped object that allows easy liquid flow throughout its structure and at the electrode membrane interface. Good contact between the disc-electrode 66 and barrier 64 is maintained simply by arranging that the one press against the other. The electrode can extend across all or part of the aqueous liquid flow path through electrode chamber 68 to provided intimate contact with the flowing aqueous stream. A conduit 70 is provided to direct the aqueous liquid stream to the inlet of electrode chamber 68. Conduit 72 takes the effluent from chamber 68 to waste.

By passing a DC current between anode 66 and cathode 62 of the electrolytic gas generator 60, a controlled amount of hydrogen gas can be generated at the device cathode 62. The amount of hydrogen gas generated is directly proportional to the applied current. Depending on the amount of oxygen gas in the incoming stream of MSA eluent, a substantially stoichiometric amount of hydrogen gas can be generated by controlling the applied current to the electrolytic gas generator. In this manner, the aqueous stream of MSA solution flowing out of the electrolytic gas generator 60 contains the substantially stoichiometric amounts of hydrogen and oxygen gases. This stream is directed into the catalytic gas elimination column 31 where hydrogen and oxygen gases react catalytically to form water. The MSA eluent stream leaving the catalytic gas elimination column is, therefore, substantially free of gas and used as the eluent in the ion chromatography process involving other down stream components.

Arranged in series with sample injector 16 and separation column 10 is a suppressor 12 serving to suppress the conductivity of the electrolyte of the eluent from column 10 but not the conductivity of the separated ions. The effluent from suppressor 12 is directed to a detector, preferably in the form of a detector flow-through conductivity cell 14, for detecting the ion species resolved in column 10.

In one embodiment, the effluent from conductivity detector 14, referred to as the detector effluent, is directed in a recycle conduit 22 to at least one flow-through detector effluent flow channel 24 in suppressor 12. An ion exchange membrane 26 separates detector effluent flow channel 24 from chromatographic separation effluent flow channel 28 which receives the effluent from chromatography column 10. In the simplified version illustrated, only a single detector effluent flow channel 24 is used. The system of the present invention is also applicable to other membrane suppressors such as the sandwich suppressor type illustrated in U.S. Pat. No. 5,248,426. In a sandwich suppressor, the chromatographic separation effluent flows through a central flow channel flanked by two detector effluent flow channels separated by ion exchange membranes. In this embodiment, the detector effluent flow channels may be supplied with the detector effluent from conductivity detector 14 by use of a splitter valve. The details of such a sandwich suppressor and the use of recycle from the conductivity cell are supplied by the detector effluent flow channel as illustrated in U.S. Pat. No. 5,248,426.

As illustrated in FIG. 3, the effluent from the suppressor effluent flow channel 24 is directed via line 30 into a cation trap column 32 which is packed with a cation exchange resin in hydronium form. The cation trap column 32 is used to remove contaminants of sample injected through injection valve 16, and other trace contaminants may be generated from operation of the ion chromatography system.

The system of FIG. 3 is also applicable to the generation of a base eluent with appropriate reversal of polarity of the reagents and charged components for anion analysis.

In the above embodiments of the present invention, water formed by the catalytic combination of hydrogen and oxygen gas can serve as a source of water for the eluent stream by flowing the produced water into the eluent stream. The gases can be electrolytically generated in the chromatography system or supplied from independent sources of hydrogen and oxygen gas such as from pressurized containers.

The following examples demonstrate the present invention for systems in which the eluents are prepared off-line and recycled and water is used in the electrolytic eluent preparation in ion chromatography.

EXAMPLE 1

Ion Chromatographic Separation of Common Anions Using an Electrolytic Suppressor and Recycle of a Sodium Carbonate/Sodium Bicarbonate Eluent This example illustrates the use of the eluent-recycle ion chromatography system shown in FIG. 1 for determination of common anions including chloride, nitrate, and sulfate. A Dionex® ICS-1500 ion chromatography system consisting of an isocratic dual-piston high pressure pump, a six-port injector, a column oven, and a conductivity detector was used. A Dionex 4-mm AS4A SC column was used as the separation column, a solution of 3 mM sodium carbonate was used as the eluent, and the separation was performed at 1.5 mL/min. A Dionex anion Atlas® electrolytic suppressor was used in the experiments. The catalytic gas elimination column was prepared by packing small strips of porous Pt foil in a ⅛ OD×1/16 ID×40 cm plastic column. The eluent purification column was packed with ion exchange resins as described previously. In one set of experiments, a sample solution containing chloride, nitrate and sulfate was injected daily. The retention time and chromatographic efficiency of each analyte were monitored over a period of 500 hours during which a 2-liter solution of 3 mM sodium carbonate was recycled continuously in the system setup shown in FIG. 1.

Reproducibility data was plotted for the retention time obtained for chloride over a period of 500 hours of continuous operation. The average retention time determined for chloride was 1.202 minutes and the percent RSD (relative standard deviation) of chloride retention time was less than 0.5%. During the same period of time, the average retention times were 1.822 minutes for nitrate and 3.44 minutes for sulfate, and the percent RDS of retention times of nitrate and sulfate were less than 0.6% and 2.7% respectively These results indicate that the ion chromatography system shown in FIG. 1 can be used to perform reproducible separation of analyte ions of interest using recycled sodium carbonate eluent over an extended period of time. The operation of an ion chromatography system in such a format simplifies the system operations, minimize waste disposal, and reduce operating costs.

EXAMPLE 2

Ion Chromatographic Separation of Common Cations Using an Electrolytic Suppressor and Recycle of a Sulfuric Acid Eluent This example illustrates the use of the eluent-recycle ion chromatography system shown in FIG. 1 for determination of common cations including lithium, sodium, ammonium, potassium, magnesium, and calcium. A Dionex DX500 ion chromatography system consisting of a dual-piston high pressure pump, a six-port injector, a column oven, and a conductivity detector was used. A Dionex 4-mm CS12A column was used as the separation column, a solution of 22 mN sulfuric acid was used as the eluent, and the separation was performed at 1.0 mL/min. A Dionex cation Atlas® electrolytic suppressor was used in the experiments. In this example, the catalytic gas elimination column and the eluent purification column were not used. A Dionex TMC-1 trace metal concentrator column was used as the cation trap column placed between the outlet of the conductive cell and inlet of the suppressor regenerant chamber. In one set of experiments, a sample solution containing lithium, sodium, ammonium, potassium, magnesium, and calcium was injected daily, the retention time and chromatographic efficiency of each analyte were determined to be stable over a period of 14 days during which a 1400-mL solution of 22 mN sulfuric acid was recycled continuously. During the period of 14 days, the relative standard deviation of retention time of each analyte was less than 1.1%, and the relative standard deviation of chromatographic efficiency of each analyte was less than 2.3%.

EXAMPLE 3

Ion Chromatographic Separation of Common Cations Using an Electrolytic Suppressor and Recycle of an Eluent Containing Methanesulfonic Acid and 2-butanone (MEK, Methyl Ethyl Ketone)

This example also illustrates the use of the eluent-recycle ion chromatography system shown in FIG. 1 for determination of common cations including lithium, sodium, ammonium, potassium, magnesium, and calcium. In this example, a Dionex DX500 ion chromatography system consisting of a dual-piston high pressure pump, a six-port injector, a column oven, and a conductivity detector was used. A Dionex 4-mm CS15 column was used as the separation column, a solution of 12 mM methoanesulfonic acid (MSA) and 5% (v/v) HPLC-grade butanone was used as the eluent, and the separation was performed at 1.0 mL/min. A Dionex cation Atlas® electrolytic suppressor was used in the experiments. No eluent purification or catalytic gas elimination columns were used. A Dionex TMC-1 trace metal concentrator column was used as the cation trap column placed between the outlet of the conductive cell and inlet of the suppressor regenerant chamber. In this set of experiments, a sample solution containing chloride, nitrate and sulfate was injected daily, the retention time and peak area response of each analyte were determined to be stable over a period of 25 days during which a 1400-mL solution of 12 mM methoanesulfonic acid (MSA) and 5% (v/v) HPLC-grade butanone was recycled continuously. During the period of 24 days, the relative standard deviation of retention time of each analyte was less than 0.6%, and the relative standard deviation of chromatographic efficiency of each analyte was less than 2.0%.

The ion chromatography system shown in FIG. 1 can be used to perform reproducible separation of cations of interest using an ion chromatographic eluent containing an organic solvent that is recycled over an extended period of time. The operation of an ion chromatography system in such a format simplifies the system operations, minimize waste disposal, and reduce operating costs.

EXAMPLE 4

Ion Chromatographic Separation of Common Anions Using an Ion-Reflux Based Ion Chromatography System with the Recycle of Water Carrier Stream The major system components used in this example are shown in FIG. 2. A DX500 ion chromatographic system (Dionex Corporation, Sunnyvale, Calif.) consisting of a GP40 pump and an AS15 separator column (4-mm ID×250-length) was used. A Dionex ASRS anion suppressor (P/N 53946) was used as the suppressor. A built-in power supply in a Dionex ED40 detector was used to supply 300 mA of DC current the suppressor. A Dionex ED40 conductivity detector equipped with a flow-through conductivity cell was used to monitor the effluent from the suppressor. The eluent generation and recycle module was similar to one described in our previous studies as described in U.S. Pat. No. 6,562,628). A Dionex EG40 Eluent Generator Module was used to supply the DC current to the anode and cathode of the eluent generation and recycle module. A Dionex PeakNet 5.0 computer workstation was used for instrument control, data collection, and processing.

In one set of experiment, a 4-liter source of deionized water was used as the carrier stream, the eluent generator and recycle module was used to generate a hydroxide gradient of 1 to 100 mN KOH at 1.0 mL/min, the separation of seven common anions on the AS15 column was monitored continuously over a period of 44 days, and the water leaving the anode chamber of the eluent generator and recycle module was recycled. FIG. 4 compares the chromatograms obtained for the separation of fluoride, chloride, carbonate, sulfate, nitrate, and phosphate on the AS15 column using (1) the deionized water that was used continuously for 44 days and (2) a fresh source of deionized water. The two chromatograms overlay perfectly in terms of analyte retention time. The background conductance of the chromatogram obtained using the recycled water remained very low using the recycled water (only slightly higher than that obtained using the fresh deionized water). The conductance of the recycled water, which was also monitored continuously over the period of 44 days. The results indicate that the conductance of recycled water remained essentially unchanged over the testing period after the initial increase to 2 µS over the first 24 hours of the recycling due to the absorption of carbon dioxide from the air.

These results indicate that the ion chromatography system shown in FIG. 2 can be used to perform reproducible separation of cations of interest using water that is recycled over an extended period of time. The operation of an ion chromatography system in such a format simplifies the system operations, minimize waste disposal, and reduce operating costs.

EXAMPLE 5

Figure 5:
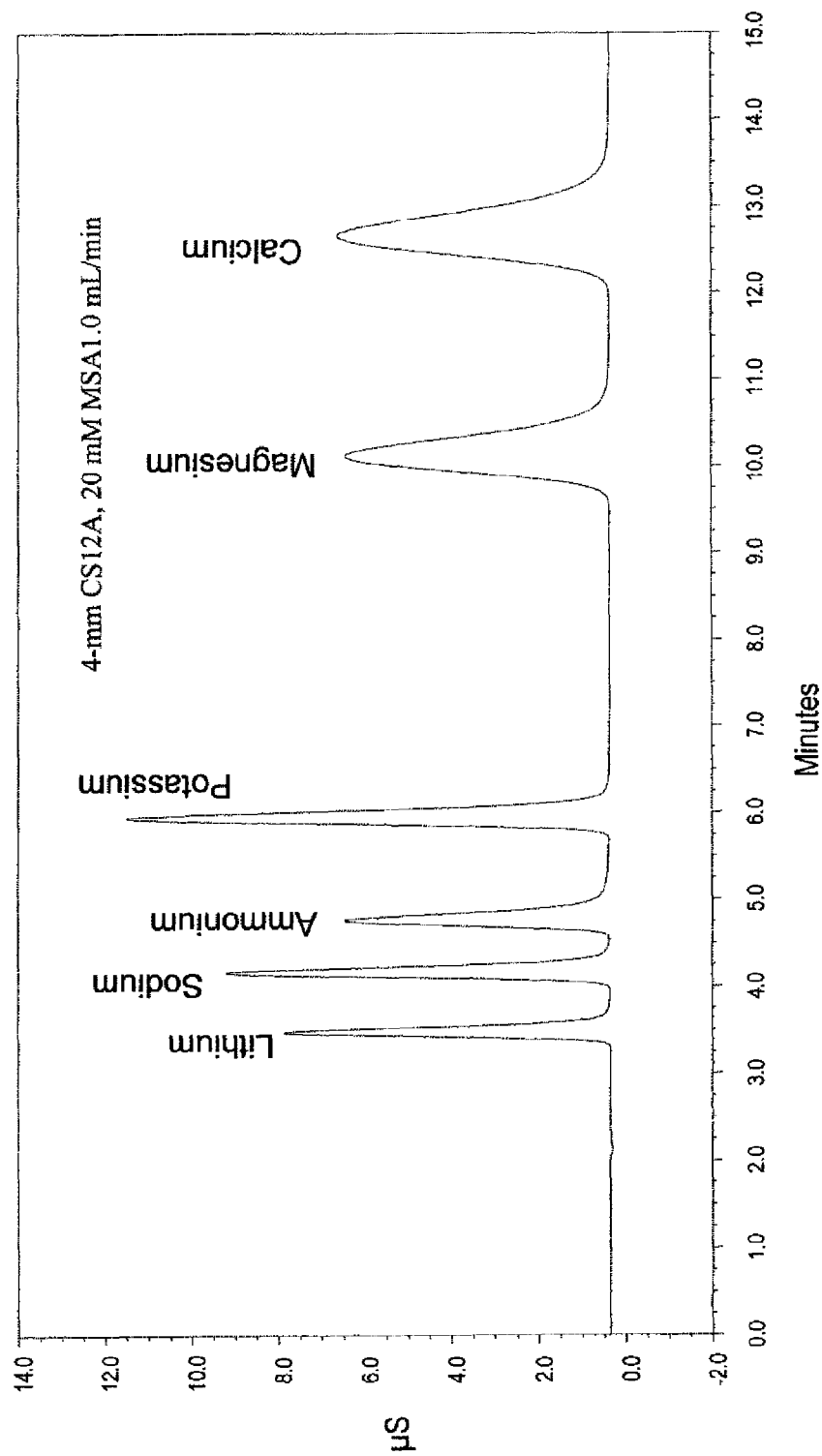

Ion Chromatographic Separation of Common Cations Using an Ion Chromatography System Equipped with an Electrolytic Gas Generation Device and a Catalytic Gas Elimination Column This example illustrates the use of the ion chromatography system shown in FIG. 3 for determination of common cations including lithium, sodium, ammonium, potassium, magnesium, and calcium. A Dionex ICS-2000 ion chromatography system consisting of an isocratic dual-piston high pressure pump, a six-port injector, a column oven, and a conductivity detector was used. A Dionex electrolytic pH modifier converted to the hydronium form was used as the electrolytic gas generator. The catalytic gas elimination column was prepared by packing small strips of Pt foil in a 4-mm ID×50-mm PEEK column. A Dionex 4-mm CS12A column was used as the separation column. A Dionex CSRS Ultra II suppressor was used in the experiments. FIG. 5 shows the separation of six common cations obtained using an ion chromatography system assembled according to FIG. 3. The separation of six cations on the CS12A column was achieved using an eluent of 20 mM MSA generated using a Dionex EGG MSA cartridge at 1.0 mL/min.

In ion chromatography system employing the methanesulfonic acid (MSA) eluent generator, oxygen gas is produced during the process of generating the MSA eluent. Oxygen gas in the MSA eluent stream leaving the eluent generator is removed typically by passing the stream through a piece of permeable tubing of the type used in Dionex EG50 eluent generator degas module (Dionex Corporation, Sunnyvale, Calif. U.S.A.). In the example, the stream of the 20-mM MSA solution containing oxygen gas was passed through the electrolytic gas generator. A DC current of 32 mA was supplied to the electrolytic gas generator to produce a stoichiometric amount of hydrogen gas relative to the amount of oxygen in the MSA eluent stream. The stream exiting the electrolytic gas generator was then passed through the catalytic gas elimination column where the stoichiometric amounts of hydrogen and oxygen gases reacted catalytically to form water. The MSA eluent stream leaving the catalytic gas elimination column was therefore free of gas and used as the eluent in the ion chromatography process involving other down stream components. The results shown in FIG. 5 indicate that the ion chromatography system shown in FIG. 3 can be used to perform ion chromatographic separation of target analyte ions.

The invention claimed is:

1. A chromatographic method comprising:
   (a) chromatographically separating sample ionic species in an aqueous liquid eluent stream flowing through a chromatography separation medium, to form a chromatography effluent,
   (b) suppressing the chromatography effluent from step (a) by flowing it through a chromatography effluent flow channel on one side of a first ion exchange membrane in a membrane suppressor,
   (c) flowing suppressor effluent from said chromatography effluent flow channel past a flow-through detector to form a detector effluent stream,
   (d) recycling the detector effluent from step (c) to a detector effluent flow channel in said membrane suppressor on the opposite side of said first membrane from said chromatography effluent flow channel,
   (e) mixing effluent from said detector effluent flow channel with a source of eluent and flowing the mixture to said chromatography separation medium, and
   (f) catalytically combining hydrogen and oxygen gas, or catalytically decomposing hydrogen peroxide, or both, in said detector effluent stream in a catalytic gas elimination chamber to form water thereby reducing the gas content in said detector effluent stream.

2. The method of claim 1 further comprising the step of:
   (f) at least partially removing ionic components in said detector effluent stream prior to mixing with said eluent source.

3. The method of claim 1 further comprising the step of:
mixing said detector effluent stream with eluent from an eluent source prior to flowing through said separation medium.

* * * * *